United States Patent [19]

Grubbs et al.

[11] Patent Number: 5,710,298
[45] Date of Patent: Jan. 20, 1998

[54] METHOD OF PREPARING RUTHENIUM AND OSMIUM CARBENE COMPLEXES

[75] Inventors: Robert H. Grubbs, South Pasadena; SonBinh T. Nguyen, Pasadena, both of Calif.; Lynda K. Johnson, Carrboro, N.C.

[73] Assignee: California Institute of Technology, Pasadena, Calif.

[21] Appl. No.: 708,057

[22] Filed: Aug. 30, 1996

Related U.S. Application Data

[63] Continuation of Ser. No. 282,826, Jul. 29, 1994, abandoned, which is a continuation-in-part of Ser. No. 106,292, Aug. 13, 1993, Pat. No. 5,342,909, which is a division of Ser. No. 863,606, Apr. 3, 1992, Pat. No. 5,312,940.

[51] Int. Cl.$^6$ ............................................. C07F 15/00
[52] U.S. Cl. .................... 556/22; 556/136; 502/155; 526/171; 526/943; 585/511; 585/643
[58] Field of Search ............................. 556/22, 136

[56] References Cited

U.S. PATENT DOCUMENTS

| | | | |
|---|---|---|---|
| 4,883,851 | 11/1989 | Grubbs et al. | 526/268 |
| 4,945,135 | 7/1990 | Grubbs et al. | 525/338 |
| 4,945,141 | 7/1990 | Grubbs et al. | 526/90 |
| 4,945,144 | 7/1990 | Grubbs et al. | 526/268 |
| 5,198,511 | 3/1993 | Brown-Wensley et al. | 526/113 |
| 5,296,566 | 3/1994 | Brown-Wensley et al. | 526/171 |
| 5,312,940 | 5/1994 | Grubbs et al. | 556/136 |
| 5,342,909 | 8/1994 | Grubbs et al. | 526/171 |

OTHER PUBLICATIONS

Burrell et al., "Synthesis and Reactions of Ru(×CH$_2$) Cl(NO) PPh$_3$)$_2$," A Stable Terminal Methylene Complex and the Crystal Structure of Ru (CH$_2$PPh$_3$)$_2$ (n$^2$–C$_2$F$_4$) Cl (NO) (PPh$_3$), J. Chem. Soc. Dalton Trans., 1991, pp. 609–614.
Ivin, K.J. "Olefin Metathesis", 1983, pp. 34–39.
McGrath et al., "Aqueous Ring–Opening Metathesis Polymerization of 7–Oxanorbornene Derivatives Using Ruthenium Catalysts", 1990, pp. 525–536.
Novak et al., "Catalytic Organometalic Chemistry in Water: The Aqueous Ring–Opening Metathesis Polymerization of 7–Oxanorbornene Derivatives", 1988, JACS, vol. 110.
Novak et al., "The Ring Opening Metathesis Polymerization of 7–Oxabicyclo [2.2.2] hept–5–ene Derivatives: A New Acyclic Polymeric Ionophere", 1988, JACS, vol. 110.
Hillmyer et al., "The Aqueous Ring–Opening Metathesis Polymerization of exo–N–Methyl–7–oxabicyclo [2.2.1] hept–5–ene–2, 3–dicarbonximide" 1991.
Carter et al., "Review of the Chemistry of Cyclopropane Compounds", Apr. 20, 1964,pp. 34–36.

Schmidbaur et al., "Ylide Chemistry: An Account of Structural, Conformational and Redox Investigations" 1983.
"Metathesis of Functionalized Olefin", J. of Molecules Catalysis, 15 (1982), pp. 35–45.
Collman et al., J. Am. Chem. Soc., vol. 108, pp. 1332–1333 (1986).
Bruce et al., "Cyclopentadienyl–Ruthenium and –osmium Chemistry, Some Reactions of Substituted Vinylidene Complexes," J. Organometallic Chem. 171:C5–C8 (1979).
M.H.L. Green et al., "Carbene Complexes of Iron, Molybdenum and Ruthenium: A New Route to Metal–Carbene Derivatives," J. Chem. Soc. (A) 794–797 (1971).
H. Le Bozec et al., "A New Route to Vinylcarbene Metal Complexes in One Step from 2–Propyn–1–ols and Arene Ruthenium(∥∥) Derivatives," J. Chem. Soc. Chem. Comm. 219–221 (1989).
Nguyen et al., "Ring–Opening Metathesis Polymerization (ROMP) of Norbornene by a Group VIII Carbene Complex in Protic Media," J. Am. Chem. Soc. 114: 3974–3975 (1992).
Grundy et al., "Migratory–Insertion Reactions of Osmium (II) Ethyl Complexes Derived From an Osmium (0) Ethylene Complex," J. Organometallic Chem. 216:255–262 (1981).
Grundy et al., "Propionyl Complexes of Ruthenium Derived From the Reaction of Ethylene with RhHCl(CO)$_2$(PPh$_3$)$_2$ J. Organometallic Chem." 265:77–85 (1984).

*Primary Examiner*—Mark Nagumo
*Attorney, Agent, or Firm*—Limbach & Limbach L.L.P.

[57] ABSTRACT

Methods of preparing carbene compounds of the formula

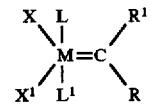

are disclosed wherein M is Os or Ru; R and R$^1$ are independently selected from hydrogen and a functional group selected from the group consisting of C$_2$–C$_{20}$ alkenyl, C$_2$–C$_{20}$ alkynyl, C$_1$–C$_{20}$ alkyl, aryl, C$_1$–C$_{20}$ carboxylate, C$_2$–C$_{20}$ alkoxy, C$_2$–C$_{20}$ alkenyloxy, C$_2$–C$_{20}$ alkynyloxy, aryloxy, C$_2$–C$_{20}$ alkoxycarbonyl, C$_1$–C$_{20}$ alkylthio, C$_1$–C$_{20}$ alkylsulfonyl or C$_1$–C$_{20}$ alkylsulfinyl; each optionally substituted with C$_1$–C$_5$ alkyl, a halogen, C$_1$–C$_5$ alkoxy or with a phenyl group optionally substituted with a halogen, C$_1$–C$_5$ alkyl or C$_1$–C$_5$ alkoxy; X and X$^1$ are independently selected from any anionic ligand; and L and L$^1$ are independently selected from any neutral electron donor, preferably phosphine, sulfonated phosphine, phosphite, phosphinite, phosphonite, arsine, stibine, ether, amine, amide, sulfoxide, carboxyl, nitrosyl, pyridine and thioether. Methods for using these carbene compounds to catalyze olefin metathesis reactions are also disclosed.

25 Claims, No Drawings

METHOD OF PREPARING RUTHENIUM AND OSMIUM CARBENE COMPLEXES

CROSS-REFERENCE TO RELATED APPLICATIONS

This is a continuation of application Ser. No. 08/282,826 filed on Jul. 29, 1994, now abandoned, which is a continuation-in-part of application Ser. No. 08/106,292, filed Aug. 13, 1993 (now U.S. Pat. No. 5,342,909) which was a divisional of application Ser. No. 07/863,606 filed Apr. 3, 1992 (now U.S. Pat. No. 5,312,940).

ORIGIN OF INVENTION

The U.S. Government has certain rights in this invention pursuant to Grant No. CHE-8922072 awarded by the National Science Foundation.

BACKGROUND OF THE INVENTION

This invention relates to the synthesis of new ruthenium and osmium metal carbene complex compounds and their use as catalysts in olefin metathesis reactions.

During the past two decades, research efforts have enabled an in-depth understanding of the olefin metathesis reaction as catalyzed by early transition metal complexes. In contrast, the nature of the intermediates and the reaction mechanism for Group VIII transition metal catalysts has remained elusive. In particular, the oxidation states and ligation of the ruthenium and osmium metathesis intermediates are not known.

Many ruthenium and osmium metal carbenes have been reported in the literature (for example, see Burrell, A. K., Clark, G. R., Rickard, C. E. F., Roper, W. R., Wright, A. H., *J. Chem. Soc.*, Dalton Trans., 1991, Issue 1, pp. 609–614). The discrete ruthenium and osmium carbene complexes isolated to date do not exhibit metathesis activity. (Ivin, *Olefin Metathesis*, pp. 34–36, Academic Press: London, 1983)

SUMMARY OF THE INVENTION

The present invention relates to the synthesis of ruthenium or osmium carbene compounds which can be used to catalyze olefin metathesis reactions.

The carbene compounds of the present invention are the only Ru and Os carbene complexes known to date in which the metal is formally in the +2 oxidation state, have an electron count of 16, and are pentacoordinate. Unlike most metathesis catalysts presently known which are poisoned by functional groups, the carbene compounds of the present invention are stable in the presence of alcohol, thiol, ketone, aldehyde, ester, ether, amine, amide, nitro acid, carboxylic acid, disulfide, carbonate, carboalkoxy and halogen functional groups and may therefore be used in protic or aqueous solvent systems.

Specifically, the present invention relates to carbene compounds of the formula

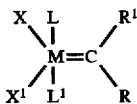

wherein:

M is Os or Ru;

R and $R^1$ are independently selected from hydrogen or a functional group selected from the group consisting of $C_2$–$C_{20}$ alkenyl, $C_2$–$C_{20}$ alkynyl, $C_1$–$C_{20}$ alkyl, aryl, $C_1$–$C_{20}$ carboxylate, $C_2$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl or $C_1$–$C_{20}$ alkylsulfinyl;

X and $X^1$ are independently selected from any anionic ligand; and

L and $L^1$ are independently selected from any neutral electron donor, preferably phosphine, sulfonated phosphine, phosphite, phosphinite, phosphonite, arsine, stibine, ether, amine, amide, sulfoxide, carboxyl, nitrosyl, pyridine and thioether, most preferably trialkylphosphine ligands where at least one of the alkyl groups is a secondary alkyl or a cycloalkyl.

In a preferred embodiment the functional group is substituted with $C_1$–$C_5$ alkyl, halogen, $C_1$–$C_5$ alkoxy or with a phenyl group.

In a preferred embodiment the phenyl group is substituted with halogen, $C_1$–$C_5$ alkyl or $C_1$–$C_5$ alkoxy.

In one embodiment of the present invention, the carbene compounds can be in the form wherein 2, 3 or 4 of the moieties X, $X^1$, L and $L^1$ can be taken together to form a chelating multidentate ligand. In one aspect of this embodiment, X, L, and $L^1$ can be taken together to form a cyclopentadienyl, indenyl, or fluorenyl moiety.

In a second, preferred embodiment of the present invention, L and $L^1$ are each trialkyl phosphine ligands where at least one of the alkyl groups is a secondary alkyl or a cycloalkyl. Carbene compounds where L and $L^1$ ligands are alkyl phosphines where the carbon backbone of at least one alkyl group of the alkyl phosopine is a secondary alkyl or cycloalkyl have been found to possess higher metathesis activity, enabling these compounds to coordinate to and catalyze metathesis reactions between all types of olefins. By contrast, previous metathesis catalysts were only able to catalyze metathesis reactions involving highly strained olefins. As a result, a broad array of metathesis reactions are enabled using the carbene compounds of the present invention that cannot be performed using less reactive catalysts. The carbene compounds of this preferred embodiment and their use in olefin metathesis reactions is described in U.S. patent application Ser. No. 08/282,827, pending entitled HIGH ACTIVITY RUTHENIUM AND OSMIUM METAL CARBENE COMPLEXES FOR OLEFIN METATHESIS REACTIONS, filed the same data as this application and which is incorporated herein by reference.

The ruthenium and osmium carbene compounds may be prepared by reacting a compound of the formula $(XX^1ML_nL^1_m)_p$, in the presence of solvent, with a cyclopropene of the formula

wherein:

M, X, $X^1$, L, and $L^1$ having the same meaning as indicated above;

n and m are independently 0–4, provided n+m=2, 3 or 4;

p is an integer equal to or greater than 1; and $R^2$ and $R^3$ are independently selected from hydrogen or a functional group selected from the group consisting of $C_1$–$C_{18}$ alkyl, $C_2$–$C_{18}$ alkenyl, $C_2$–$C_{18}$ alkynyl, $C_2$–$C_{18}$ alkoxycarbonyl, aryl, $C_1$–$C_{18}$ carboxylate, $C_1$–$C_{18}$ alkenyloxy, $C_2$–$C_{18}$ alkynyloxy, $C_1$–$C_{18}$ alkoxy, aryloxy, $C_1$–$C_{18}$ alkylthio, $C_1$–$C_{18}$ alkylsulfonyl or $C_1$–$C_{18}$ alkylsulfinyl;

In a preferred embodiment the hydrocarbon is substituted with $C_1$–$C_5$ alkyl, halogen, $C_1$–$C_3$ alkoxy or with a phenyl group.

In a preferred embodiment the phenyl group is substituted with halogen, $C_1$–$C_5$ alkyl or $C_1$–$C_5$ alkoxy.

In one embodiment of the process, X, L, and $L^1$ are taken together to form a moiety selected from the group consisting of cyclopentadienyl, indenyl or fluorenyl, each optionally substituted with hydrogen; $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl, $C_1$–$C_{20}$ alkylsulfinyl; each optionally substituted with $C_1$–$C_5$ alkyl, halogen, $C_1$–$C_5$ alkoxy or with a phenyl group optionally substituted with halogen, $C_1$–$C_5$ alkyl or $C_1$–$C_5$ alkoxy.

A further method of preparing the compounds of this invention comprises reacting compound of the formula $(XX^1ML_nL^1_m)_p$ in the presence of solvent with a phosphorane of the formula

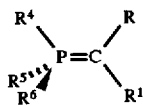

wherein:

M, X, $X^1$, L, $L^1$, n, m, p, R, and $R^1$ have the same meaning as indicated above; and $R^4$, $R^5$ and $R^6$ are independently selected from aryl, $C_1$–$C_6$ alkyl, $C_1$–$C_6$ alkoxy or phenoxy, each optionally substituted with halogen, $C_1$–$C_3$ alkyl, $C_1$–$C_3$ alkoxy, or with a phenyl group optionally substituted with halogen, $C_1$–$C_5$ alkyl or $C_1$–$C_5$ alkoxy.

The present invention also pertains to a preferred method of preparing the aforementioned ruthenium and osmium compounds comprising reacting $[(Ar) MX X^1]_2$ dimer complex with two equivalents of a phosphine ligand and a cyclopropene of the formula

in a one step synthesis wherein:

M, X and $X^1$ have the same meaning as indicated above;

Ar is an aromatic compound, preferably a di-, tri-, tetra- or hexa- substituted benzene, most preferably selected from benzene, toluene, xylene, cymene, tetramethylbenzene or hexamethylbenzene; and phosphine ligand is represented by the formula $PR^7R^8R^9$ wherein $R^7$, $R^8$ and $R^9$ are independently selected from substituted and unsubstituted $C_1$–$C_{10}$ alkyl, secondary alkyl, cycloalkyl and aryl.

Another embodiment of the present invention comprises preparing compounds of Formula II and Formula III

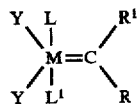

-continued

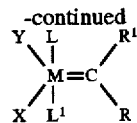

from compound of Formula I

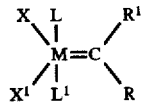

comprising reacting said compound of Formula I, in the presence of solvent, with compound of the formula $M^1Y$ wherein:

M, R, $R^1$ X, $X^1$, L, and $L^1$ have the same meaning as indicated above, and wherein:

(1) $M^1$ is Li, Na or K, and Y is $C_1$–$C_{10}$ alkoxide, arylalkoxide, amide or arylamide each optionally substituted with $C_1$–$C_{10}$ alkyl or halogen, diaryloxide; or (2) $M^1$ is Na or Ag, and Y is $ClO_4$, $PF_6$, $BF_4$, $SbF_6$ halogen, $B(aryl)_4$, $C_1$–$C_{10}$ alkyl sulfonate or aryl sulfonate.

Another embodiment of the present invention is a method of preparing compounds of structures of Formula IV

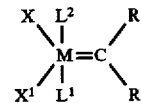

and Formula V

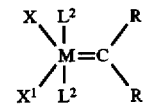

from a compound of Formula I

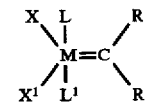

comprising reacting a compound of Formula I, in the presence of solvent, with $L^2$ wherein:

M, R, $R^1$, X, and $X^1$ have the same meaning as indicated above; and

L, $L^1$, and $L^2$ are independently selected from any neutral electron donor, preferably secondary alkyl or cycloalkyl phosphine ligands.

The compounds of Formulae II, III, IV, and V are species of, i.e., fall within, the scope of compounds of Formula I. In other words, certain compounds of Formula I are used to form other compounds of Formula I by ligand exchange. In this case, X and $X^1$ in Formula I are other than the Y in Formulae II and III that replaces X. Similarly, L and $L^1$ in Formula I are other than the $L^2$ in Formulae IV and V. If any 2 or 3 of X, $X^1$, L, and $L^1$ form a multidentate ligand of Formula I, only the remaining ligand moieties would be available for ligand replacement.

The reference above to X, $X^1$, L, and $L^1$ having the same meaning as indicated above refers to these moieties individually and taken together to form a multidentate ligand as described above.

DETAILED DESCRIPTION

The ruthenium and osmium carbene complexes of the invention are useful for catalyzing olefin metathesis reactions. The propagating carbene moiety has been found to be stable and continues to polymerize additional aliquots of monomer for a period after the original amount of monomer has been consumed. The propagating carbene moiety has also been found to be stable in the presence of alcohol, thiol, ketone, aldehyde, ester, ether, amine, amide, nitro acid, carboxylic acid, disulfide, carbonate, carboalkoxy and halogen functional groups. Aspects of this invention include the metal carbene compounds, methods for their synthesis, as well as their use as catalysts in a wide variety of olefin metathesis reactions.

The intermediate compounds $(XX^1ML_nL^1_m)_p$ are either available commercially or can be prepared by standard known methods.

The phosphorane and cyclopropene reactants used in the present invention may be prepared in accordance with the following respective references. Schmidbaur, H. et at., *Phosphorus and Sulfur*, Vol. 18, pp. 167–170 (1983); Carter, F. L., Frampton, V. L., *Chemical Reviews*, Vol. 64, No. 5 (1964) which are incorporated herein by reference.

With regard to compounds of Formula I:

alkenyl can include 1-propenyl, 2-propenyl; 3-propenyl and the different butenyl, pentenyl and hexenyl isomers, 1,3-hexadienyl and 2,4,6-heptatrienyl, and cycloalkenyl;

alkenyloxy can include $H_2C=CHCH_2O$, $(CH_3)_2C=CHCH_2O$, $(CH_3)CH=CHCH_2{}^\wedge O$ $(CH_3)CH=C(CH_3)CH_2O$ and $CH_2=CHCH_2CH_2O$;

alkoxide can include methoxide, t-butoxide, and phenoxide;

alkoxy can include methoxy, ethoxy, n-propyloxy, isopropyloxy and the different butoxy, pentoxy and hexyloxy isomers, cycloalkoxy can include cyclopentyloxy and cyclohexyloxy;

alkoxyalkyl can include $CH_3OCH_2$, $CH_3OCH_2CH_2$, $CH_3CH_2OCH_2$, $CH_3CH_2CH_2CH_2OCH_2$ and $CH_3CH_2OCH_2CH_2$; and alkoxycarbonyl can include $CH_3OC(=O)$; $CH_3CH_2OC(=O)$, $CH_3CH_2CH_2OC(=O)$, $(CH_3)_2CHOC(=O)$ and the different butoxy-, pentoxy- or hexyloxycarbonyl isomers;

alkyl can include primary, secondary and cycloalkyl isomers;

alkylsulfinyl can include $CH_3SO$, $CH_3CH_2SO$, $CH_3CH_2CH_2SO$, $(CH_3)_2CHSO$ and the different butylsulfinyl, pentylsulfinyl and hexylsulfinyl isomers;

alkylsulfonyl can include $CH_3SO_2$, $CH_3CH_2SO_2$, $CH_3CH_2CH_2SO_2$, $(CH_3)_2CHSO_2$ and the different butylsulfonyl, pentylsulfonyl and hexylsulfonyl isomers;

alkylthio can include, methylthio, ethylthio, and the several propylthio, butylthio, pentylthio and hexylthio isomers;

alkynyl can include ethynyl, 1-propynyl, 3-propynyl and the several butynyl, pentynyl and hexynyl isomers, 2,7-octadiynyl and 2,5,8-decatriynyl;

alkynyloxy can include $HC=CCH_2O$, $CH_3C=CCH_2O$ and $CH_3C=CCH_2OCH_2O$;

amide can include $HC(=O)N(CH_3)_2$ and $(CH_3)C(=O)N(CH_3)_2$;

amine can include tricyclohexylamine, triisopropylamine and trineopentylamine;

arsine can include triphenylarsine, tricyclohexylarsine and triisopropylarsine;

aryl can include phenyl, p-tolyl and p-fluorophenyl;

carboxylate can include $CH_3CO_2CH_3CH_2CO_2$, $C_6H_5CO_2$, $(C_6H_5)CH_2CO_2$;

cycloalkenyl can include cyclopentenyl and cyclohexenyl;

cycloalkyl can include cyclopropyl, cyclobutyl, cyclopentyl, and cyclohexyl;

diketonates can include acetylacetonate and 2,4-hexanedionate;

ether can include $(CH_3)_3CCH_2OCH_2CH_3$, THF, $(CH_3)_3COC(CH_3)_3$, $CH_3OCH_2CH_2OCH_3$, and $CH_3OC_6H_5$;

"halogen" or "halide", either alone or in compound words such as "haloalkyl", denotes fluorine, chlorine, bromine or iodine;

phosphine can include triphenylphosphine, tricyclohexylphosphine, triisopropylphosphine, trineopentylphosphine and methyldiphenylphosphine;

phosphinite can include triphenylphosphinite, tricyclohexylphosphinite, triisopropylphosphinite, and methyldiphenylphosphinite;

phosphite can include triphenylphosphite, tricyclohexylphosphite, tri-t-butylphosphite, triisopropylphosphite and methyldiphenylphosphite;

secondary alkyl includes ligands of the general formula —CHRR$^1$ where R and R$^1$ are carbon moieties;

stibine can include triphenylstibine, tricyclohexylstibine and trimethylstibine;

sulfonate can include trifluoromethanesulfonate, tosylate, and mesylate;

sulfoxide can include $CH_3S(=O)CH_3$, $(C_6H_5)_2SO$; and thioether can include $CH_3SCH_3$, $C_6H_5SCH_3$, $CH_3OCH_2CH_2SCH_3$, and tetrahydrothiophene.

A neutral electron donor is any ligand which, when removed from a metal center in its closed shell electron configuration, has a neutral charge, i.e., is a Lewis base.

An anionic ligand is any ligand which when removed from a metal center in its closed shell electron configuration has a negative charge. An important feature of the carbene compounds of this invention is the presence of the ruthenium or osmium in the formal +2 oxidation state (the carbene fragment is considered to be neutral), an electron count of 16 and pentacoordination. A wide variety of ligand moieties X, X$^1$, L, and L$^1$ can be present and the carbene compound will still exhibit its catalytic activity.

A preferred embodiment of the carbene compounds of the present invention is:

A compound of the invention of Formula I wherein:

R and R$^1$ are independently selected from hydrogen, vinyl, $C_1$–$C_{10}$ alkyl, aryl, $C_1$–$C_{10}$ carboxylate, $C_2$–$C_{10}$ alkoxycarbonyl, $C_1$–$C_{10}$ alkoxy, aryloxy, each optionally substituted with $C_1$–$C_5$ alkyl, halogen, $C_1$–$C_5$ alkoxy or with a phenyl group optionally substituted with halogen, $C_1$–$C_5$ alkyl or $C_1$–$C_5$ alkoxy;

X and X$^1$ are independently selected from halogen, hydrogen, diketonates, or $C_1$–$C_{20}$ alkyl, aryl, $C_1$–$C_{20}$ alkoxide, aryloxide, $C_2$–$C_{20}$ alkoxycarbonyl, arylcathoxylate, $C_1$–$C_{20}$ carboxylate, aryl or $C_1$–$C_{20}$ alkylsulfonate, $C_1$–$C_{20}$ alkylthio, $C_1$–$C_{20}$ alkylsulfonyl, $C_1$–$C_{20}$ alkylsulfinyl, each optionally substituted with $C_1$–$C_5$ alkyl, halogen, $C_1$–$C_5$ alkoxy or with a phenyl group optionally substituted with halogen, $C_1$–$C_5$ alkyl or $C_1$–$C_5$ alkoxy; and L and L$^1$ are independently selected from phosphine, sulfonated phosphine, phosphite, phosphinite, phosphonite, arsine, stibine, ether, amine, amide, surfoxide, carbonyl, nitrosyl, pyridine or thioether.

A more preferred embodiment of the carbene compounds of the present invention is:

A compound of Formula I wherein:

R and R$^1$ are independently selected from hydrogen; vinyl, C$_1$–C$_5$ alkyl, phenyl, C$_2$–C$_5$ alkoxycarbonyl, C$_1$–C$_5$ carboxylate, C$_1$–C$_5$ alkoxy, phenoxy; each optionally substituted with C$_1$–C$_5$ alkyl, halogen, C$_1$–C$_5$ alkoxy or a phenyl group optionally substituted with halogen, C$_1$–C$_5$ alkyl or C$_1$–C$_5$ alkoxy;

X and X$^1$ are independently selected from Cl, Br, I, or benzoate, acetylacetonate, C$_1$–C$_5$ carboxylate, C$_1$–C$_5$ alkyl, phenoxy, C$_1$–C$_5$ alkoxy, C$_1$–C$_5$ alkylthio, aryl, and C$_1$–C$_5$ alkyl sulfonate; each optionally substituted with C$_1$–C$_5$ alkyl or a phenyl group optionally substituted with halogen, C$_1$–C$_5$ alkyl or C$_1$–C$_5$ alkoxy;

L, and L$^1$ are independently selected from aryl or C$_1$–C$_{10}$ alkylphosphine or C$_1$–C$_5$ alkyl, secondary alkyl or cycloalkylphosphine, aryl- or C$_1$–C$_{10}$ alkylsulfonated phosphine, aryl or C$_1$–C$_{10}$ alkylphosphinite, aryl- or C$_1$–C$_{10}$ alkylphosphonite, aryl- or C$_1$–C$_{10}$ alkylphosphite, aryl- or C$_1$–C$_{10}$ alkylarsine, aryl- or C$_1$–C$_{10}$ alkylamine, pyridine, aryl- or C$_1$–C$_{10}$ alkyl sulfoxide, aryl- or C$_1$–C$_{10}$ alkylether, or aryl- or C$_1$–C$_{10}$ alkylamide, each optionally substituted with a phenyl group optionally substituted with halogen, C$_1$–C$_5$ alkyl or C$_1$–C$_5$ alkoxy.

A further preferred embodiment of the present invention is carbene compounds of Formula I wherein:

R and R$^1$ are independently vinyl, H, Me, Ph;

X and X$^1$ are independently Cl, CF$_3$CO$_2$, CH$_3$CO$_2$, CFH$_2$CO$_2$, (CH$_3$)$_3$CO, (CF$_3$)$_2$(CH$_3$)CO, (CF$_3$)(CH$_3$)$_2$CO, PhO, MeO, EtO, tosylate, mesylate, or trifluoromethanesulfonate; and L and L$^1$ are independently PPh$_3$, P(p-Tol)$_3$, P(o-Tol)$_3$, PPh(CH$_3$)$_2$, P(CF$_3$)$_3$, P(p-FC$_6$H$_4$)$_3$, pyridine, P(p-CF$_3$C$_6$H$_4$)$_3$, (p-F)pyridine, (p-CF$_3$)pyridine, P(C$_6$H$_4$-SO$_3$Na)$_3$, P(CH$_2$C$_6$H$_4$-SO$_3$Na)$_3$, P($^i$Pr)$_3$, P(CHCH$_3$(CH$_2$CH$_3$))$_3$, P(cyclopentyl)$_3$, P(cyclohexyl)$_3$, P(neopentyl)$_3$, P(Me)$_3$, PMe(Ph)$_2$ and P(neophenyl)$_3$.

For any of the foregoing described preferred groups of compounds, any 2, 3, or 4 of X, X$^1$, L, L$^1$ can be taken together to form a chelating multidentate ligand. Examples of bidentate ligands include, but are not limited to, bisphosphines, dialkoxides, alkyldiketonates, and aryldiketonates. Specific examples include Ph$_2$PCH$_2$CH$_2$PPh$_2$, Ph$_2$AsCH$_2$CH$_2$AsPh$_2$, Ph$_2$PCH$_2$CH$_2$C(CF$_3$)$_2$O—, binaphtholate dianions, pinacolate dianions, Me$_2$P(CH$_2$)$_2$PMe$_2$ and —OC(CH$_3$)$_2$(CH$_3$)$_2$CO—. Tridentate ligands include, but are not limited to, (CH$_3$)$_2$NCH$_2$CH$_2$P(Ph)CH$_2$CH$_2$N(CH$_3$)$_2$. Other preferred tridentate ligands are those in which X, L, and L$^1$ are taken together to be cyclopentadienyl, indenyl or fluorenyl, each optionally substituted with C$_2$–C$_{20}$ alkenyl, C$_2$–C$_{20}$ alkynyl, C$_1$–C$_{20}$ alkyl, aryl, C$_1$–C$_{20}$ carboxylate, C$_1$–C$_{20}$ alkoxy, C$_2$–C$_{20}$ alkenyloxy, C$_2$–C$_{20}$ alkynyloxy, aryloxy, C$_2$–C$_{20}$ alkoxycarbonyl, C$_1$–C$_{20}$ alkylthio, C$_1$–C$_{20}$ alkylsulfonyl, C$_1$–C$_{20}$ alkylsulfinyl, each optionally substituted with C$_1$–C$_5$ alkyl, halogen, C$_1$–C$_5$ alkoxy or with a phenyl group optionally substituted with halogen, C$_1$–C$_5$ alkyl or C$_1$–C$_5$ alkoxy. More preferably in compounds of this type, X, L, and L$^1$ are taken together to be cyclopentadienyl or indenyl, each optionally substituted with hydrogen; vinyl, C$_1$–C$_{10}$ alkyl, aryl, C$_1$–C$_{10}$ carboxylate, C$_2$–C$_{10}$ alkoxycarbonyl, C$_1$–C$_{10}$ alkoxy, aryloxy, each optionally substituted with C$_1$–C$_5$ alkyl, halogen, C$_1$–C$_5$ alkoxy or with a phenyl group optionally substituted with halogen, C$_1$–C$_5$ alkyl or C$_1$–C$_5$ alkoxy. Most preferably, X, L, and L$^1$ are taken together to be cyclopentadienyl, optionally substituted with vinyl, hydrogen, Me or Ph. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

Carbene compounds of Formula I wherein L and L$^1$ are alkyl phosphines where at least one alkyl group is either a secondary alkyl or a cycloalkyl. These carbene compounds have been found to be more stable, more reactive to non-sterically strained cyclic alkenes and unreactive to a wider variety of substituents. (Nguyen, S., et al., *J. Am. Chem. Soc.*, 1993, 115:9858–9859; Fu, G., et al., *J. Arm Chem. Soc.*, 1993, 115:9856–9557.)

Specifically, carbene compounds wherein L and L$^1$ are triisopropyl phosphine or tricyclohexyl phosphine have been found to be stable in the presence of oxygen; moisture, adventitious impurities thereby enabling reactions to be conducted in reagent grade solvents in air (Fn, G., et al., *J. Am. Chem. Soc.*, 1993, 115:9856–9857). Further these carbenes are stable in the presence of alcohol thiol, ketone, aldehyde, ester, ether, amine, amide, nitro acid, carboxylic acid, disulfide, carbonate, carboalkoxy and halogen functional groups. In addition, these carbene can catalyze olefin metathesis reactions on acyclic olefins and strained cyclic olefins.

The most preferred carbene compounds of the present invention include:

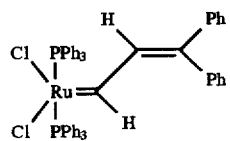

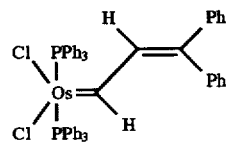

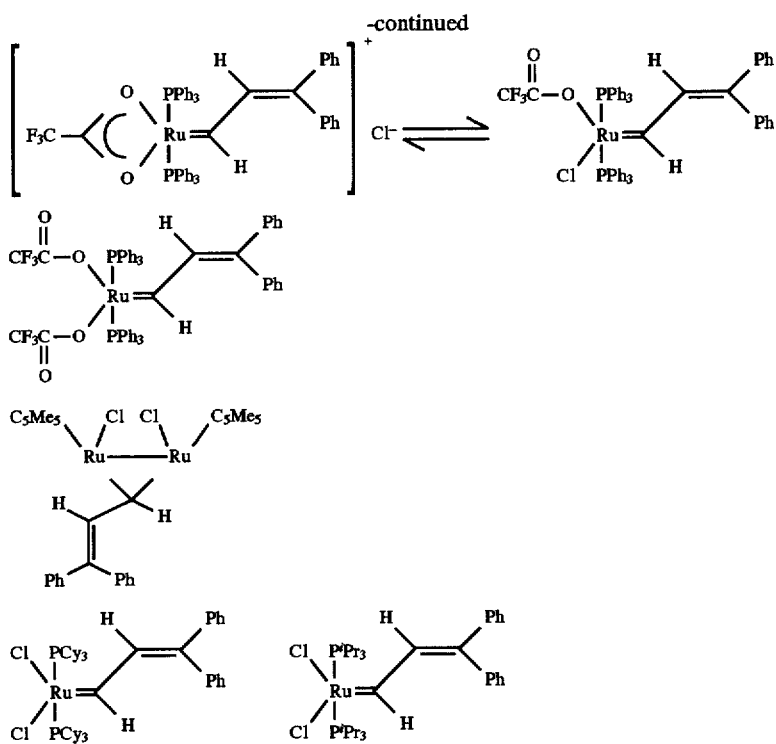

$^i$Pr=isopropyl
Cy=cyclohexyl

The compounds of the present invention can be prepared in several different ways, each of which is described below.

The most general method for preparing the compounds of this invention comprises reacting $(XX^1ML_nL^1_m)_p$ with a cyclopropene or phosphorane in the presence of a solvent to produce a carbene complex, as shown in the equations below.

REACTION EQUATIONS

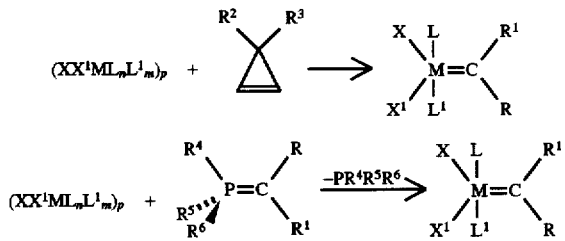

wherein:

M, X, $X^1$, L, $L^1$, n, m, p, $R^2$, $R^3$, $R^4$, $R^5$, and $R^6$ are as defined above. Preferably, $R^2$, $R^3$, $R^4$, $R^5$, and $R^6$ are independently selected from the group consisting of $C_1$–$C_6$ alkyl or phenyl.

Examples of solvents that may be using in this reaction include organic, protic, or aqueous solvents which are inert under the reaction conditions, such as: aromatic hydrocarbons, chlorinated hydrocarbons, ethers, aliphatic hydrocarbons, alcohols, water, or mixtures thereof. Preferred solvents include benzene, toluene, p-xylene, methylene chloride, dichloroethane, dichlorobenzene, tetrahydrofuran, diethylether, chlorobenzene, pentane, methanol, ethanol, water, or mixtures thereof. More preferably, the solvent is benzene, toluene, p-xylene, methylenechloride, dichloroethane, dichlorobenzene, tetrahydrofuran, diethylether, pentane, chlorobenzene, methanol, ethanol, or mixtures thereof. Most preferably, the solvent is toluene or a mixture of benzene and methylene chloride.

A suitable temperature range for the reaction is from about −20° C. to about 125° C., preferably 35° C. to 90° C., and more preferably 50° C. to 65° C. Pressure is not critical but may depend on the boiling point of the solvent used, i.e., sufficient pressure is needed to maintain a solvent liquid phase. Reaction times are not critical, and can be from several minutes to 48 hours. The reactions are generally carried out in an inert atmosphere, most preferably nitrogen or argon.

The reaction is usually carried out by dissolving the compound $(XX^1ML_nL^1_m)_p$ in a suitable solvent, adding the cyclopropene (preferably in a solvent) to a stirred solution of the compound, and optionally heating the mixture until the reaction is complete. The progress of the reaction can be monitored by any of several standard analytical techniques, such as infrared or nuclear magnetic resonance. Isolation of the product can be accomplished by standard procedures, such as evaporating the solvent, washing the solids (e.g., with alcohol or pentane), and then recrystallizing the desired carbene complex. Whether the moieties X, $X^1$, L, or $L^1$ are (unidentate) ligands or taken together to form multidentate ligands will depend on the starting compound which simply carries these ligands over into the desired carbene complex.

Under certain circumstances no solvent is needed.

In one variation of this general procedure, the reaction is conducted in the presence of $HgCl_2$, preferably 0.01 to 0.2 molar equivalents, more preferably 0.05 to 0.1 equivalents, based on $XX^1ML_nL^1_m$. In this variation, the reaction temperature is preferably 15° C. to 65° C.

In a second variation of the general procedure, the reaction is conducted in the presence of ultraviolet radiation. In this variation, the reaction temperature is preferably −20° C. to 30° C.

It is also possible to prepare carbene complexes of this invention by ligand exchange. For example, L and/or $L^1$ can be replaced by a neutral electron donor, $L^2$, in compounds of Formula I by reacting $L^2$ with compounds of Formula I wherein L, $L^1$, and $L^2$ are independently selected from phosphine, sulfonated phosphine, phosphite, phosphinite, phosphorrite, arsine, stibine, ether, amine, amide, sulfoxide, carbonyl, nitrosyl, pyridine or thioether. Similarly, X and/or $X^1$ can be replaced by an anionic ligand, Y, in compounds of Formula I by reacting $M^1Y$ with compounds of Formula I, wherein Y, X and $X^1$ are independently selected from halogen, hydrogen, diketonates, or $C_1$-$C_{20}$ alkyl, aryl, $C_1$-$C_{20}$ alkoxide, aryloxide, $C_2$-$C_{20}$ alkoxycarbonyl, arylcalboxylate, $C_1$-$C_{20}$ carboxylate, aryl or $C_1$-$C_{20}$ alkylsulfonate, $C_1$-$C_{20}$ alkylthio, $C_1$-$C_{20}$ alkylsulfonyl, $C_1$-$C_{20}$ alkylsulfinyl, each optionally substituted with $C_1$-$C_5$ alkyl, halogen, $C_1$-$C_5$ alkoxy or with a phenyl group optionally substituted with halogen, $C_1$-$C_5$ alkyl or $C_1$-$C_5$ alkoxy. These ligand exchange reactions are typically carried out in a solvent which is inert under the reaction conditions. Examples of solvents include those described above for the preparation of the carbene complex.

The carbene compounds of the present invention may also be prepared by a one step synthesis as shown in equation below

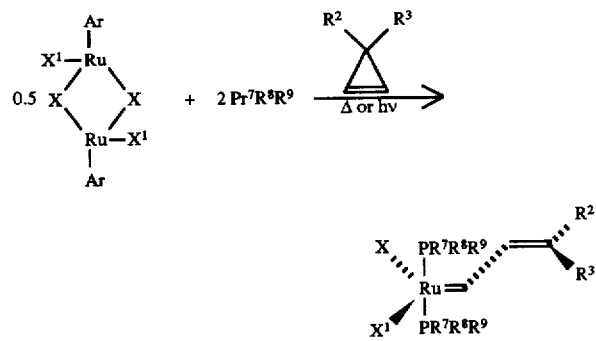

wherein M, X, $X^1$, $R^2$ and $R^3$ are as defined above. Preferably, $R^2$ and $R^3$ are independently selected from the group consisting of $C_1$-$C_6$ alkyl or phenyl. Ar represents an aromatic compound, preferably a di-, tri-, tetra- or hexa-substituted benzene, most preferably benzene, toluene, xylene, cymene, tetramethylbenzene and hexamethylbenzene. $R^7$, $R^8$ and $R^9$ are independently selected from substituted and unsubstituted $C_1$-$C_{10}$ alkyl, secondary alkyl, cycloalkyl and aryl.

Examples of solvents for this reaction include benzene, toluene, xylene and cymene. A suitable temperature range for this reaction is from about 0° C. to about 120° C., preferably 45° C. to 90° C. The reaction may be conducted in the presence of oxygen. However, it is preferred that it is carried out under an inert atmosphere. The reaction is generally performed under atmospheric pressure. Monitoring the progression of the reaction and isolation of the product can be accomplished by any one of a variety of standard procedures known in the art as described above. Typical reaction conditions for this one step synthesis are provided in Example 11.

The carbene compounds of the present invention may be employed in a variety of olefin metathesis reactions such as those described in U.S. Pat. No. 5,312,940 which is incorporated by reference herein and co-pending U.S. patent application, Ser. No. 08/282,827, pending entitled "high Activity Ruthenium and Osmium Carbene Complexes for Olefin Metathesis", entitled HIGH ACTIVITY RUTHENIUM AND OSMIUM METAL CARBENE COMPLEXES FOR OLEFIN METATHESIS REACTIONS, filed on the same date as this application and which is also incorporated herein by reference.

The following examples set forth the synthesis and application of the ruthenium and osmium carbene compounds of the present invention. The following examples also set forth the preferred embodiments of the present invention. Further objectives and advantages of the present invention other than those set forth above will become apparent from the examples which are not intended to limit the scope of the present invention.

The abbreviations Me, Ph, $^i$Pr, Cy and THF used in the following examples refer to methyl, phenyl, isopropyl, cyclohexyl, and tetrahydrofuran, respectively.

EXAMPLES

1. Method of Preparing Compounds of This Invention From Cyclopropene

A 50 mL Schlenk flask equipped with a magnetic stirbar is charged with $(MXX^1L_nL^1{}_m)_p$ (0.1 mmol) inside a nitrogen-filled drybox. Methylene chloride (2 mL) is added to dissolve the complex followed by 25 mL of benzene to dilute the solution. One equivalent of a cyclopropene is then added to the solution. The reaction flask is then capped with a stopper, removed from the box, attached to a reflux condenser under argon and heated at 55° C. The reaction is then monitored by NMR spectroscopy until all the reactants have been converted to the product. At the end of the reaction, the solution is allowed to cool to room temperature under argon and filtered into another Schlenk flask via a cannula filter. The solvent is then removed in vacuo to give a solid. This solid is then washed with a solvent in which the by-product of the reaction is soluble but the desired product is not. After the washing the product, the supernatant is removed and the resulting solid powder is dried in vacuo overnight. Further purification via crystallization can be performed if necessary.

Representative compounds of the present invention which may be prepared in accordance with the procedure described above are exemplified in Table 1.

TABLE 1

$$\begin{matrix} X & L & & R \\ & \backslash | & & \\ & M & = & \\ & /| & & \\ X^1 & L^1 & & R^1 \end{matrix}$$

| Compound name | M | X | X$^1$ | L | L$^1$ | R | R$^1$ |
|---|---|---|---|---|---|---|---|
| Dichloro-3,3-diphenylvinylcarbene-bis-(triphenylphosphine)ruthenium(II) | Ru | Cl | Cl | PPh$_3$ | PPh$_3$ | H | CH=CPh$_2$ |
| Dibromo-3,3-diphenylvinylcarbene-bis-(triphenylphosphine)ruthenium(II) | Ru | Br | Br | PPh$_3$ | PPh$_3$ | H | CH=CPh$_2$ |
| Dichloro-3,3-diphenylvinylcarbene-bis-(methyldiphenylphosphine)ruthenium(II) | Ru | Cl | Cl | PPh$_2$Me | PPh$_2$Me | H | CH=CPh$_2$ |
| Dibromo-3,3-diphenylvinylcarbene-bis-(methyldiphenylphosphine)ruthenium(II) | Ru | Br | Br | PPh$_2$Me | PPh$_2$Me | H | CH=CPh$_2$ |
| Dichloro-3-methyl-3-phenylvinylcarbene-bis-(triphenylphosphine)ruthenium(II) | Ru | Cl | Cl | PPh$_3$ | PPh$_3$ | H | CH=CPhMe |
| Dibromo-3-methyl-3-phenylvinylcarbene-bis-(triphenylphosphine)ruthenium(II) | Ru | Br | Br | PPh$_3$ | PPh$_3$ | H | CH=CPhMe |
| Dichloro-3,3-dimethylvinylcarbene-bis-(triphenylphosphine)ruthenium(II) | Ru | Cl | Cl | PPh$_3$ | PPh$_3$ | H | CH=CMe$_2$ |
| Bisacetato-3,3-diphenylvinylcarbene-bis-(triphenylphosphine)ruthenium(II) | Ru | O$_2$CMe | O$_2$CMe | PPh$_3$ | PPh$_3$ | H | CH=CPh$_2$ |
| Acetatochloro-3,3-dimethylvinylcarbene-bis-(triphenylphosphine)ruthenium(II) | Ru | O$_2$CMe | Cl | PPh$_3$ | PPh$_3$ | H | CH=CPh$_2$ |
| 3,3-diphenylvinylcarbene-bis-(trifluoroacetato)-bis-(triphenylphosphine)ruthenium(II) | Ru | O$_2$CCF$_3$ | O$_2$CCF$_3$ | PPh$_3$ | PPh$_3$ | H | CH=CPh$_2$ |
| 3,3-diphenylvinylcarbene-η$^3$-pinacol bis-(triphenylphosphine)ruthenium(II) | Ru | 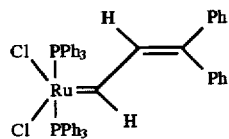 | | PPh$_3$ | PPh$_3$ | H | CH=CPh$_2$ |
| 3,3-diphenylvinylcarbene-bis-(tert-butoxy)bis-(triphenylphosphine)ruthenium(II) | Ru | OCMe$_3$ | OCMe$_3$ | PPh$_3$ | PPh$_3$ | H | CH=CPh$_2$ |
| 3,3-diphenylvinylcarbene-bis-(2-trifluoromethyl-2-propoxy bis-(triphenylphosphine)ruthenium | Ru | Me\|Me\\CO/F$_3$C | Me\|Me\\CO/F$_3$C | PPh$_3$ | PPh$_3$ | H | CH=CPh$_2$ |

These are representative examples of the ruthenium complexes. Analogous complexes can be made with osmium.

2. Synthesis of:

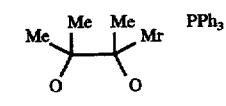

In a typical reaction, a 200 mL Schlenk flask equipped with a magnetic stirbar was charged with RuCl$_2$(PPh$_3$)$_4$ (6.00 g, 4.91 mmol) inside a nitrogen-filled drybox. Methylene chloride (40 mL) was added to dissolve the complex followed by 100 mL of benzene to dilute the solution. 3,3-Diphenylcyclopropene (954 mg, 1.01 equiv) was then added to the solution via pipette. The reaction flask was capped with a stopper, removed from the box, attached to a reflux condenser under argon and heated at 53° C. for 11 h. After allowing the solution to cool to room temperature, all the solvent was removed in vacuo to give a dark yellow-brown solid. Benzene (10 mL) was added to the solid and subsequent swirling of the mixture broke the solid into a fine powder. Pentane (80 mL) was then slowly added to the mixture via cannula while stirring vigorously. The mixture was stirred at room temperature for 1 h and allowed to settle before the supernatant was removed via cannula filtration. This washing procedure was repeated twice more to ensure the complete removal of all phosphine by-products. The resulting solid was then dried under vacuum overnight to afford 4.28 g (98%) of Compound 1 as a yellow powder with a slight green tint. $^1$H NMR (C$_6$D$_6$): δ 17.94 (pseudo-quartet=two overlapping triplets, 1H, Ru=C$\underline{H}$, J$_{HH}$=10.2 Hz, J$_{PH}$=9.7 Hz), 8.70 (d, 1H, C$\underline{H}$=CPh$_2$, J$_{HH}$ 10.2 Hz). $^{31}$P NMR (C$_6$D$_6$): δ 28.2 (s). $^{13}$C NMR (CD$_2$Cl$_2$): δ 288.9 (t, M=$\underline{C}$, J$_{CP}$=10.4 Hz) 149.9 (t, C$\underline{H}$=CPh$_2$, J$_{CP}$=11.58 Hz).

The carbene complex which is the compound formed in the above example is stable in the presence of water, alcohol, acetic acid, HCl in ether and benzaldehyde.

3. Synthesis of:

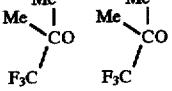

A 50 mL Schlenk flask equipped with a magnetic stirbar was charged with OsCl$_2$(PPh$_3$)$_3$ (100 mg, 0.095 mmol) inside a nitrogen-filled drybox. Methylene chloride (2 mL) was added to dissolve the complex followed by 25 mL of benzene to dilute the solution. 3,3-diphenylcyclopropene (18.53 mg, 1.01 equiv) was then added to the solution via pipet. The reaction flask was capped with a stopper, removed from the box, attached to a reflux condenser under argon and heated at 55° C. for 14 h. After allowing the solution to cool to room temperature, all the solvent was removed in vacuo to give a dark yellow-brown solid. Benzene (2 mL) was added to the solid and subsequent swirling of the mixture broke the solid into a fine powder. Pentane (30 mL) was then slowly added to the mixture via cannula while stirring vigorously. The mixture was stirred at room temperature for 1 h and allowed to settle before the supernatant was removed via cannula filtration. This washing procedure was repeated two more times to ensure the complete removal of all phosphine by-products. The resulting solid was then dried under vacuum overnight to afford 74.7 mg of $Cl_2(PPh_3)_2Os$ (=CHCH=CPh$_2$) as a yellow powder (80%). $^1$H NMR ($C_6D_6$): δ 19.89 (pseudo-quartet=two overlapping triplets, 1H, Os=C$\underline{H}$, $J_{HH}$=10.2 Hz), 8.23 (d, 1H, C$\underline{H}$=CPh$_2$, $J_{HH}$=10.2 Hz). $^{31}$P NMR ($C_6D_6$): δ 4.98 (s).

4. Synthesis of:

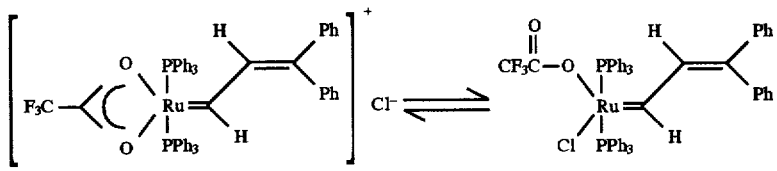

A 50 mL Schlenk flask equipped with a magnetic stirbar was charged with $RuCl_2(PPh_3)_2$(=CHCH=CPh$_2$) (100 mg, 0.18 mmol) inside a nitrogen-filled drybox. Methylene chloride (10 mL) was added to dissolve the complex. $AgCF_3CO_2$ (24.9 mg, 1 equiv) was weighed into a 10 ml round-bottom flask, dissolved with 3 ml of THF. Both flasks were then capped with rubber septa and removed from the box. The Schlenk flask was then put under an argon atmosphere and the $AgCF_3CO_2$ solution was added dropwise to this solution via a gas-tight syringe over a period of 5 min while stirring. At the end of the addition, there was a lot of precipitate in the reaction mixture and the solution turned into a fluorescent green color. The supernatant was transferred into another 50 mL Schlenk flask under argon atmosphere via the use of a cannula filter. Subsequent solvent removal in vacuo and washing with penme (10 mL) afforded a green solid powder of the above depicted compound. Yield=92.4 mg (85%). $^1$H NMR (2:2:1 $CD_2Cl_2:C_6D_6$:THF-d$_8$): δ 18.77 (dt, 1H, Ru=C$\underline{H}$, $J_{HH}$=11.2 Hz, $J_{PH}$=8.6 Hz), 8.40 (d, 1H), C$\underline{H}$=CPh$_2$, $J_{HH}$=11.2 Hz). $^{31}$P NMR (2:2:1 $CD_2Cl_2:C_6D_6$:THF-d$_8$): δ 29.4. $^{19}$F NMR (2:2:1 $CD_2Cl_2:C_6D_6$:THF-d$_8$): δ 75.8.

5. Synthesis of:

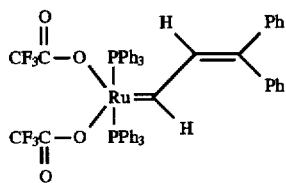

A 50 mL Schlenk flask equipped with a magnetic stirbar was charged with $RuCl_2(PPh_3)_2$(=CH—CH=CPh$_2$) (100 mg, 0.11 mmol) inside a nitrogen-filled drybox. Methylene chloride (10 mL) was added to dissolve the complex. $AgCF_3CO_2$ (49.8 mg, 2 equiv) was weighed into a 10 mL round-bottom flask, dissolved with 4 mL of THF. Both flasks were then capped with rubber septa and removed from the box. The Schlenk flask was then put under an argon atmosphere and the $AgCF_3CO_2$ solution was added dropwise via a gas tight syringe over a period of 5 min to the solution of ruthenium compound while stirring. At the end of the addition, there was a lot of precipitate in the reaction mixture and the solution turned into a fluorescent lime green color. The supernatant was transferred into another 50 mL Schlenk flask under argon atmosphere with the use of a cannula filter. Subsequent solvent removal in vacuo and washing with pentane (10 mL) afforded the above depicted compound as a green powder. Yield=102 mg (87%) $^1$H NMR (2:2:1 $CD_2Cl_2:C_6D_6$:THF-d$_8$) δ 19.23 (dt, slightly overlapping) Ru=C$\underline{H}$, $J_{HH}$=11.5 Hz, $J_{PH}$=5.4 Hz), 8.07 (d, 1H, C$\underline{H}$=CPH2, $J_{HH}$=11.5 Hz). $^{31}$P NMR (2:2:1 $CD_2Cl_2:C_6D_6$:THF-d$_8$): δ 28.6. $^{19}$F NMR (2:2:1 $CD_2Cl_2:C_6D_6$:THF-d$_8$): δ −75.7.

6. Synthesis of:

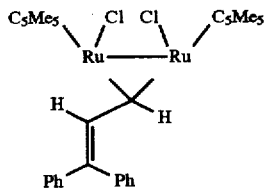

The reaction between [Ru(C$_5$Me$_5$)Cl]$_4$ and 3,3-diphenylcyclopropene was done under a nitrogen atmosphere. [Ru(C$_5$Me$_5$)Cl]$_4$ (100 mg, 0.092 mmoL) was dissolved in 10 mL of tetrahydrofuran. To this solution was added 3,3-diphenylcyclopropene (350 mg, 1.82 mmol). The resulting solution was stirred at room temperature for 1 h. Petroleum ether (10 mL) was then added to the reaction mixture. The reaction was stirred for an additional 30 min, after which all volatile components were removed from the reaction mixture under vacuum. The crude product was extracted with diethyl ether; volatiles were removed from the filtrate under vacuum to afford a dark colored, oily solid. The crude product was further extracted with petroleum ether; volatiles were removed from the filtrate under vacuum to afford a very dark red-brown oil. Recrystallization from petroleum ether at −40° C. afforded dark crystals. The NMR spectra of the product was consistent with the formulation [(C$_5$Me$_5$)RuCl]$_2$ (=CH—CH=CPh$_2$).

7. Polymerization of Norbornene Using Compound of Example 2

$(PPh_3)_2Cl_2Ru$=CH—CH=CPh$_2$ catalyzed the polymerization of norbornene in a 1:8 mixture of $CH_2Cl_2/C_6H_6$ at room temperature to yield polynorbornene. A new signal, attributed to H$_\alpha$ of the propagating carbene, was observed by $^1$H NMR spectroscopy at 17.79 ppm. Its identity and stability was confirmed by preparing a block polymer with 2,3-dideuteronorbornene and perprotionorbornene. When 2,3-dideuteronorbornene was added to the propagating species, the new carbene signal vanished and then reappeared when perprotionorbornene was added for the third block.

8. Polymerization of Norbornene Using Compound of Example 6

[(C₅Me₅)RuCl]₂(=CH—CH—CPh₂) (14 mg, 0.030 mmol) was dissolved in 1 mL of perdeuterated toluene under a nitrogen atmosphere. To this was added norbornene (109 mg, 1.16 mmol). The reaction mixture became viscous within minutes as the norbornene polymerized. After 20 h at room temperature a ¹H NMR spectrum of the reaction mixture was taken, which showed polynorbornene and unreacted norbornene monomer in a ratio of 82:12.

9. Synthesis of:

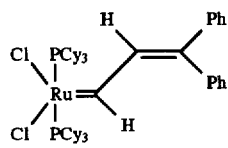

In a typical reaction, a 100 mL Schlenk flask equipped with a magnetic stirbar was charged with (Ph₃P)₂Cl₂Ru=CH—CH=CPh₂ (3.624 g, 4.08 mmol) and PCy₃ (2.4 g, 2.1 equiv) inside a nitrogen-filled drybox. Methylene chloride (60 mL) was added to dissolve the mixture. The reaction flask was capped with a stopper, removed from the drybox, and stirred under argon overnight during which time the reaction mixture turned red. The reaction mixture was then cannula-filtered under argon into another Scklenk flask. The red filtrate was then concentrated under in vacuo to about 15 mL. Pentane (60 mL) was slowly added to the mixture via cannula while stirring vigorously. A flocculent green solid, consisting mostly starting material, begins to be separated out of the solution when about 40 mL of penme is added. The red supernatant was quickly transferred into another Schlenk flask via cannula filtration and then evaporated to dryness under in vacuo. The remaining red solid was washed with pentane (3×40 mL). To ensure the complete removal of all phosphine by-products, each wash was stirred at room temperature for at least 30 minutes before the supernatant was cannula-filtered away. The resulting solid was then dried under vacuum overnight to afford 3.39 g (ca. 90%) of (Cy₃P)₂Cl₂Ru=CH—CH=CPh₂ as a red powder.

10. Ring-Closing Metathesis of Functionalized Dienes

Table 2 depicts the synthesis of several cycloalkenes from functionalized dienes using Cl₂Ru(PCy₃)₂(=CCH=CPh₂) wherein Cy is cyclohexyl. A typical experimental procedure for performing ring-closing metathesis on the diene of entry 8 of Table 2 is as follows.

The diene of entry 8 (0.50 mmol) was added to a homogeneous orange-red solution of 0.01 mmol Cl₂Ru (PCy₃)₂(=CCH=CPh₂) in 15 mL of dry benzene under argon. The resulting mixture was then stirred at 20° C. for 5 h, at which time thin layer chromatography showed the reaction to be complete. The reaction was then quenched by exposure to air (until greenish-black, 6 h), concentrated and purified by flash chromatography (0→6% Et₂O/hexane) to yield dihydropyran as a colorless oil in 86% yield.

TABLE 2

Catalytic Ring-Closing Metathesis of Dienes (2–4 mol % [Ru]m C₆H₆, 20° C.)

| entry | substrate | product | time (hours) | yield (%) |
|---|---|---|---|---|
| 1 X = CF₃ | | | 1 | 93 |
| 2   Ot-Bu | | | 1 | 91 |
| 3 | | | 1 | 89 |
| 4 n = 0 | | | 22 | 78 |
| 5   1 | | | 6 | 93 |
| 6   2 | | | 40 | 81 |

TABLE 2-continued

Catalytic Ring-Closing Metathesis of Dienes (2-4 mol % [Ru]m C₆H₆, 20° C.)

| entry | substrate | product | time (hours) | yield (%) |
|---|---|---|---|---|
| 7 | (allyl-O-CH(Ph)-vinyl) | 2,5-dihydrofuran with Ph | 2 | 84 |
| 8 | (allyl-O-CH(Ph)-CH₂-allyl) | 3,6-dihydro-2H-pyran with Ph | 5 | 86 |
| 9 | (allyl-O-CH₂-CH(Ph)-allyl) | 7-membered O-ring with Ph | 8 | 72 |
| 10 | (diallyl acetal of PhCH₂CHO) | 7-membered dioxepine with CH₂Ph | 1 | 87 |
| 11 | (diene-OTBS) | cyclopentene-OTBS | 2 | 85 |

11. One Step Synthesis of Carbene Compounds

The carbene compounds of the present invention may be prepared in a one step synthesis as illustrated in the reaction sequence below.

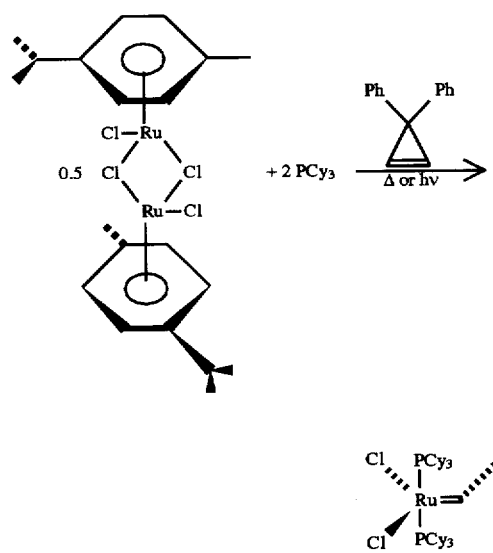

In a typical reaction, [(Cymene)RuCl₂]₂ dimer complex (0.53 g, 1.73 mmol Ru) and PCy₃ (0.91 g, 2 equiv) were loaded under inert atmosphere into a 100 mL Schlenk flask equipped with a magnetic stirbar. Benzene(40 mL) was then added followed by 3,3-diphenylcyclopropene(0.33g, 1 equiv). The reaction flask was then attached to a reflux condenser under an inert atmosphere and heated in an oilbath at 83°–85° C. for 6 hours. The solvent was then removed to complete dryness in vacuo and the remaining red solid washed with penme (4×25 mL) under inert atmosphere. The remaining red powder was dried under vacuum for 12 h and stored under an inert atmosphere yielding 1.4 g of Cl₂Ru(PCy₃)₂(=CCH=CPh₂) in 88% yield.

12. Carbene Catalyzed Polymerization of 5-Acetoxy-cyclooctene

The carbene compounds of the present invention may be used in the polymerization of nonstrained cyclic olefins such as cyclooctene as depicted in the reaction sequence below.

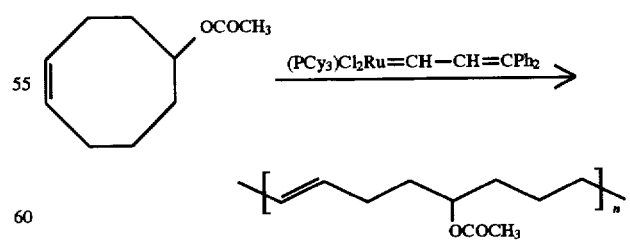

In order to polymerize 5-acetoxy-cyclooctene, a small vial was charged with 2.6 g of degassed 5-acetoxy-cyclooctene and a stirbar. A solution of 15 mg of Cl₂Ru(PCy₃)₂ (=CCH=CPh₂) in 200 µL of CH₂Cl₂ was added to the vial under inert atmosphere. The vial was capped and placed in an oil bath at about 48° C. After about 2.5 hours, the red-orange solution became noticeably viscous. After about 5.5 hours, the contents of the vial were solid. After 24 hours, the vial was removed from the oil bath and cooled to room temperature. The cap was removed from the vial and 100 μL of ethyl vinylether, 10 mL of chloroform and about 10 mg of 2,6-di-tert-butyl-4-methylphenol(butylated hydroxytoluene) were added to the vial to dissolve the solid, yielding a yellow-orange solution. After about 12 hours of stirring, an additional 20 mL of chloroform was added to the solution. The resulting solution was then poured into about 200 mL of methanol yielding an off-white precipitate. The off-white solid was stirred in the methanol until it appeared free of color. 2.2 g of the resulting white solid was then isolated and dried under vacuum in 85% yield.

While the present invention is disclosed by reference to the preferred embodiments and examples detailed above, it is to be understood that these examples are intended in an illustrative rather than limiting sense, and it is contemplated that modifications within the spirit and scope of the invention will readily occur to those skilled in the art, which modifications are intended to be encompassed within the scope of the appended claims.

What is claimed is:

1. A method of preparing a compound of formula

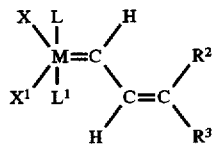

the method comprising reacting a compound of the formula $(XX^1ML_nL^1{}_m)_p$ with a cyclopropene of the formula

in the presence of a solvent wherein:

M is Os or Ru;

$R^2$ and $R^3$ are independently selected from the group consisting of hydrogen, and a substituent group selected from the group consisting of $C_1-C_{18}$ alkyl, $C_2-C_{18}$ alkenyl, $C_2-C_{18}$ alkynyl, $C_2-C_{18}$ alkoxycarbonyl, aryl, $C_1-C_{18}$ carboxylate, $C_1-C_{18}$ alkenyloxy, $C_2-C_{18}$ alkynyloxy, $C_1-C_{18}$ alkoxy, aryloxy, $C_1-C_{18}$ alkylthio, $C_1-C_{18}$ alkylsulfonyl and $C_1-C_{18}$ alkylsulfinyl; each substituent group optionally substituted with $C_1-C_5$ alkyl, halogen, $C_1-C_5$ alkoxy or with a phenyl group optionally substituted with halogen, $C_1-C_5$ alkyl or $C_1-C_5$ alkoxy;

X and $X^1$ are independently selected from the group consisting of any anionic ligand;

L and $L^1$ are independently selected from the group consisting of any neutral electron donor;

n and m are independently 0-4, provided n+m=2, 3 or 4;

p is an integer equal to or greater than 1; and any 2 or 3 of X, $X^1$, L, and $L^1$ are optionally bonded together to form a chelating multidentate ligand.

2. The method according to claim 1, wherein $R^2$ and $R^3$ are independently selected from the group consisting of $C_1-C_6$ alkyl and phenyl.

3. The method according to claim 1, wherein X and $X^1$ are independently selected from the group consisting of halogen, hydrogen, diketonates, and a substituent group selected from the group consisting of $C_1-C_{20}$ alkyl, aryl, $C_1-C_{20}$ alkoxide, aryloxide, $C_2-C_{20}$ alkoxycarbonyl, arylcarboxylate, $C_1-C_{20}$ carboxylate, aryl or $C_1-C_{20}$ alkylsulfonate, $C_1-C_{20}$ alkylthio, $C_1-C_{20}$ alkylsulfonyl, $C_1-C_{20}$ alkylsulfinyl, each substituent group optionally substituted with $C_1-C_5$ alkyl, halogen, $C_1-C_5$ alkoxy or with a phenyl group optionally substituted with halogen, $C_1-C_5$ alkyl or $C_1-C_5$ alkoxy.

4. The method according no claim 3, wherein X and $X^1$ are independently selected from the group consisting of Cl, Br, I, and a substituent group selected from the group consisting of benzoate, acetylacetonate, $C_1-C_5$ carboxylate, $C_1-C_5$ alkyl, phenoxy, $C_1-C_5$ alkoxy, $C_1-C_5$ alkylthio, aryl, and $C_1-C_5$ alkyl sulfonate; each substituent group optionally substituted with $C_1-C_5$ alkyl, halogen, $C_1-C_5$ alkoxy or a phenyl group optionally substituted with halogen, $C_1-C_5$ alkyl or $C_1-C_5$ alkoxy.

5. The method according to claim 4, wherein X and $X^1$ are independently selected from the group consisting of Cl, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate.

6. The method according to claim 1, wherein L and $L^1$ are independently selected from the group consisting of phosphine, sulfonated phosphine, phosphite, phosphinite, phosphonite, arsine, stibine, ether, amine, amide, sulfoxide, carbonyl, nitrosyl, pyridine and thioether.

7. The method according to claim 1, wherein L and $L^1$ are independently selected from the group consisting of arylphosphine, $C_1-C_{10}$ alkylphosphine, arylsulfonated phosphine, $C_1-C_{10}$ alkylsulfonated phosphine, arylphosphinite, $C_1-C_{10}$ alkylphosphinite, arylphosphonite, $C_1-C_{10}$ alkylphosphonite, arylphosphite, $C_1-C_{10}$ alkylphosphite, arylarsine, $C_1-C_{10}$ alkylarsine, arylamine, $C_1-C_{10}$ alkylamine, pyridine, arylsulfoxide, $C_1-C_{10}$ alkylsulfoxide, arylether, $C_1-C_{10}$ alkylether, arylamide, and $C_1-C_{10}$ alkylamide; each optionally substituted with a phenyl group optionally substituted with halogen, $C_1-C_5$ alkyl or $C_1-C_5$ alkoxy.

8. The method according to claim 1, wherein L and $L^1$ are independently selected from the group consisting of $PMe_3$, $PPh_3$, $P(p\text{-}Tol)_3$, $P(o\text{-}Tol)_3$, $PMePh_2$, $PPhMe_2$, $P(CF_3)_3$, $P(p\text{-}FC_6H_4)_3$, pyridine, $P(p\text{-}CF_3C_6H_4)_3$, (p-F)pyridine, (p-$CF_3$) pyridine, $P(C_6H_4\text{—}SO_3Na)_3$, and $P(CH_2C_6H_4\text{—}SO_3Na)_3$.

9. The method according to claim 1, wherein 2 of L, $L^1$, X and $X^1$ are taken together to form a bidentate ligand selected from the group consisting of bisphosphines, dialkoxides, alkyldiketonates, and aryldiketonates.

10. The method according to claim 1, wherein 2 of L, $L^1$, X and $X^1$ are taken together to form a bidentate ligand selected from the group consisting of $Ph_2PCH_2CH_2PPh_2$, $Ph_2AsCH_2CH_2AsPh_2$, $Ph_2PCH_2CH_2C(CF_3)O$—, binaphtholate dianions, pinacolate dianions, $Me_2P(CH_2)_2PMe_2$, and —$OC(CH_3)_2(CH_3)_2CO$—.

11. The method according to claim 1, wherein 3 of L, $L^1$, and X are taken together to form a tridentate ligand selected from the group consisting of cyclopentadienyl, indenyl, and fluorenyl, each optionally substituted with a substituent group selected from the group consisting of $C_2-C_{20}$ alkenyl, $C_2-C_{20}$ alkynyl, $C_1-C_{20}$ alkyl, aryl, $C_1-C_{20}$ carboxylate, $C_1-C_{20}$ alkoxy, $C_2-C_{20}$ alkenyloxy, $C_2-C_{20}$ alkynyloxy, aryloxy, $C_2-C_{20}$ alkoxycarbonyl, $C_1-C_{20}$ alkylthio, $C_1-C_{20}$ alkylsulfonyl, and $C_1-C_{20}$ alkylsulfinyl, each optionally substituted with $C_1-C_5$ alkyl, halogen, $C_1-C_5$ alkoxy or with a phenyl group optionally substituted with halogen, $C_1-C_5$ alkyl or $C_1-C_5$ alkoxy.

12. The method according to claim 11, wherein the tridentate ligand is selected from the group consisting of cyclopentadienyl or indenyl, each optionally substituted with vinyl, $C_1$–$C_{10}$ alkyl, aryl, $C_1$–$C_{10}$ carboxylate, $C_2$–$C_{10}$ alkoxycarbonyl, $C_1$–$C_{10}$ alkoxy, aryloxy, each optionally substituted with $C_1$–$C_5$ alkyl, halogen, $C_1$–$C_5$ alkoxy or with a phenyl group optionally substituted with halogen, $C_1$–$C_5$ alkyl or $C_1$–$C_5$ alkoxy.

13. The method according to claim 12, wherein the tridentate ligand is cyclopentadienyl, optionally substituted with vinyl, Me or Ph.

14. The method according to claim 1, wherein the solvent is selected from the group consisting of organic, protic, and aqueous solvents.

15. The method according to claim 1, wherein the solvent is selected from the group consisting of aromatic hydrocarbons, chlorinated hydrocarbons, ethers, aliphatic hydrocarbons, alcohols, water, and mixtures thereof.

16. The method according to claim 15, wherein the solvent is selected from the group consisting of benzene, toluene, p-xylene, methylene chloride, dichloroethane, dichlorobenzene, tetrahydrofuran, diethylether, pentate, methanol, ethanol, water, and mixtures thereof.

17. The method according to claim 15, wherein the solvent is selected from the group consisting of toluene or a mixture of benzene or methylene chloride.

18. The method according to claim 1, wherein the reaction is carried out at a temperature from about –20° C. to about 125° C.

19. The method according to claim 18, wherein the reaction is carried out at a temperature from about 35° C. to about 90° C.

20. The method according to claim 19, wherein the reaction is carried out at a temperature from about 50° C. to about 65° C.

21. The method according to claim 1, wherein the reaction of $(XX^1ML_nL^1_m)_p$ with the cyclopropene includes the steps of:

(a) dissolving the compound $(XX^1ML_nL^1_m)_p$ in the solvent to give a $(XX^1ML_nL^1_m)_p$ solution; and (b) adding the cyclopropene to the $(XX^1ML_nL^1_m)_p$ solution.

22. The method according to claim 21, wherein the reaction of $(XX^1ML_nL^1_m)_p$ with the cyclopropene includes the further steps of heating the cyclopropene/$(XX^1ML_nL^1_m)_p$ solution mixture produced in step (b).

23. The method according to claim 1, wherein the reaction of $(XX^1ML_nL^1_m)_p$ with the cyclopropene includes the steps of:

(a) dissolving the compound $(XX^1ML_nL^1_m)_p$ in the solvent to give a $(XX^1ML_nL^1_m)_p$ solution;

(b) dissolving the cyclopropene in the solvent to give a cyclopropene solution; and (c) adding the cyclopropene solution to the $(XX^1ML_nL^1_m)_p$ solution.

24. The method according to claim 1, wherein the reaction of $(XX^1ML_nL^1_m)_p$ with the cyclopropene is carried out in the presence of $HgCl_2$.

25. A method of preparing a compound of formula

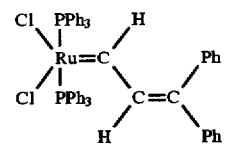

the method comprising reacting $RuCl_2(PPh_3)_4$ with 3,3-Diphenylcyclopropene in the presence of a solvent.

* * * * *